(12) United States Patent
Gillis et al.

(10) Patent No.: US 7,964,368 B2
(45) Date of Patent: Jun. 21, 2011

(54) EVALUATING BACTERIAL LETHALITY OF CONTAINERIZED FOOD PRODUCTION

(75) Inventors: John R. Gillis, Bozeman, MT (US);
Kurtis J. McCauley, Belgrade, MT (US)

(73) Assignee: SGM Biotech, Inc., Boseman, MT (US)

( * ) Notice: Subject to any disclaimer, the term of this patent is extended or adjusted under 35 U.S.C. 154(b) by 473 days.

(21) Appl. No.: 11/410,196

(22) Filed: Apr. 25, 2006

(65) Prior Publication Data

US 2006/0240504 A1   Oct. 26, 2006

Related U.S. Application Data

(60) Provisional application No. 60/674,610, filed on Apr. 25, 2005.

(51) Int. Cl.
*G01N 33/554* (2006.01)
*C12M 1/34* (2006.01)

(52) U.S. Cl. .................... 435/7.32; 435/287.4

(58) Field of Classification Search ............... 435/287.4
See application file for complete search history.

(56) References Cited

U.S. PATENT DOCUMENTS

| | | | |
|---|---|---|---|
| 3,346,464 A | 10/1967 | Ernst | |
| 3,960,670 A | 6/1976 | Pflug | |
| 4,291,122 A | 9/1981 | Orelski | |
| 4,311,793 A | 1/1982 | Halleck | |
| 5,521,094 A | 5/1996 | Narayan | |
| 5,637,475 A * | 6/1997 | Narayan | 435/31 |
| 6,121,012 A | 9/2000 | Falkowski et al. | |
| 6,340,590 B1 * | 1/2002 | Gillis | 435/287.4 |
| 6,455,272 B1 | 9/2002 | Gillis et al. | |
| 7,563,616 B2 | 7/2009 | Gillis | |

FOREIGN PATENT DOCUMENTS

| | | |
|---|---|---|
| EP | 1 201 255 A2 | 5/2002 |
| SU | 535072 | 11/1976 |
| WO | WO 03/024491 | 3/2003 |

* cited by examiner

*Primary Examiner* — Gary B. Nickol
*Assistant Examiner* — Khatol Shahnah-Shah
(74) *Attorney, Agent, or Firm* — Breiner & Breiner, L.L.C.

(57) ABSTRACT

Procedures and means for evaluating effectiveness of bacterial-lethality, following batch-processed containerized food production operations and aseptic-flow food-production operations as containerized in aseptic-containers, in preparing for non-refrigerated marketing are described. The evaluations significantly expedite determining whether thermally-processed containerized food-production is safe for non-refrigerated marketing. The presence or absence of live spore-forming bacteria is determined chemically free of extended storage requirements relying on a mechanical-failure indication of food-spoilage. Also, a biological-indication verification of microbial-biocidal status of the packaged food is made available. The invention determines whether rigid-sheet metal containers, and/or whether any of the new, and newly developing, non-refrigerated food packages, which largely utilize polymeric materials, for convenient microwave-oven heating of opened-packs, and soft polymeric pouch products, are safe for non-refrigerated marketing; and, such determinations are made substantially more concurrently with production-operations, than previously available.

9 Claims, 15 Drawing Sheets

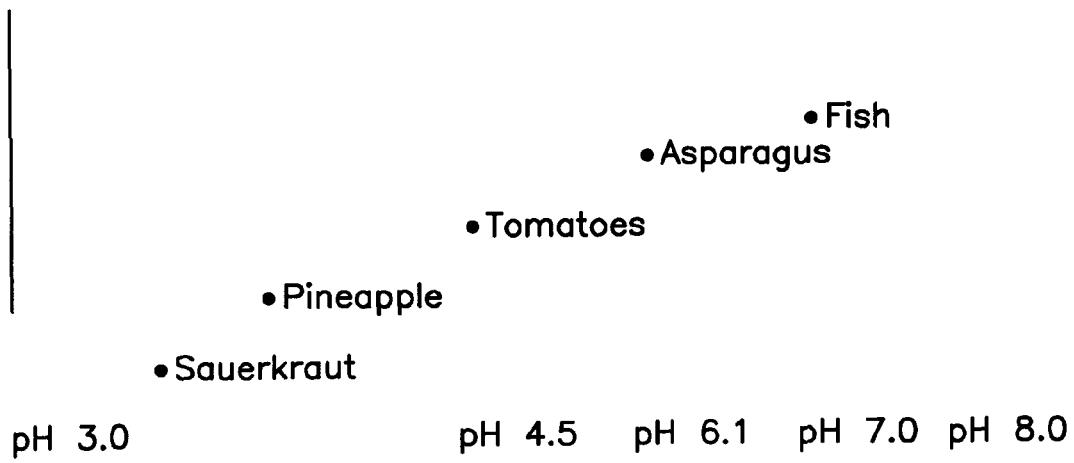
For Selecting Thermal-Exposure
for Various Batch-Processed Foods
FIG. 2
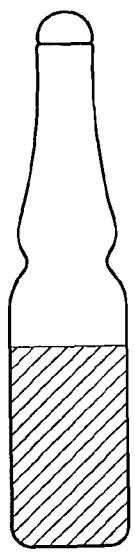
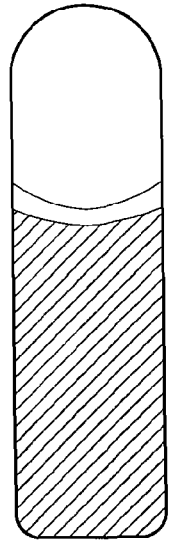
FIG. 3(a)  FIG. 3(b)

Elongated Flexible Tube
Sealed at One Longitudinal End

Hollow Configuration Filled with
Growth Medium and Test Constituents

One End of Filled Tubular
Configuration Inserted for
Forming First Ampoule

Closing Jaws of Sealer
for First Ampoule

Single Individual Filled Ampoule Formed at Sealed Longitudinal End of Tubular Configuration Five Sealed Ampoules Formed
from filled Tubular Configuration

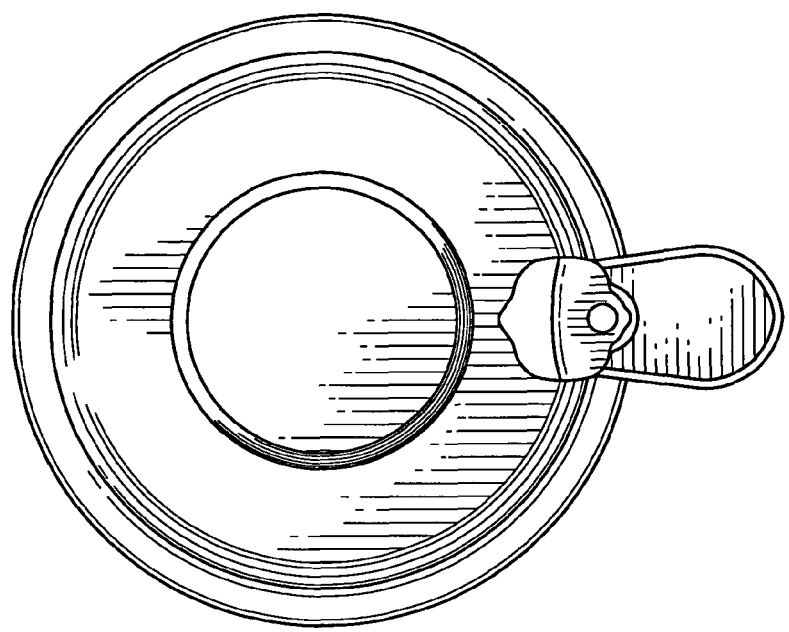
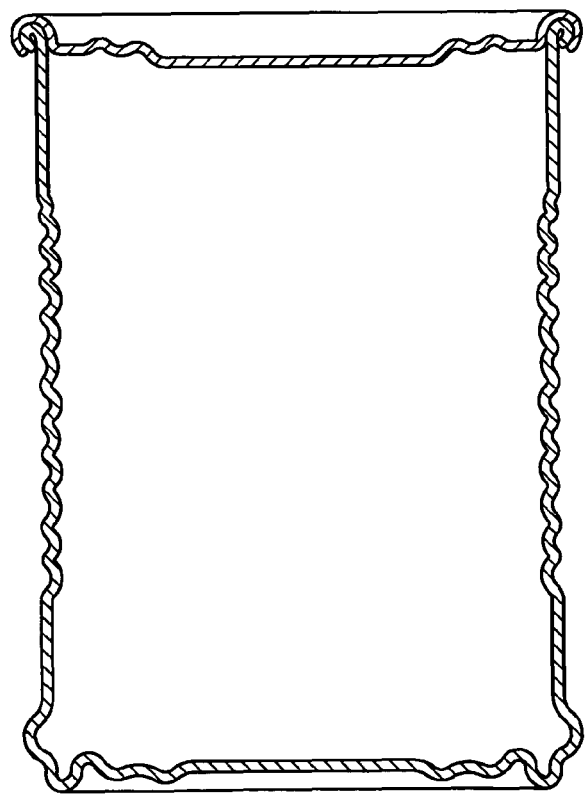
FIG. 5(a)

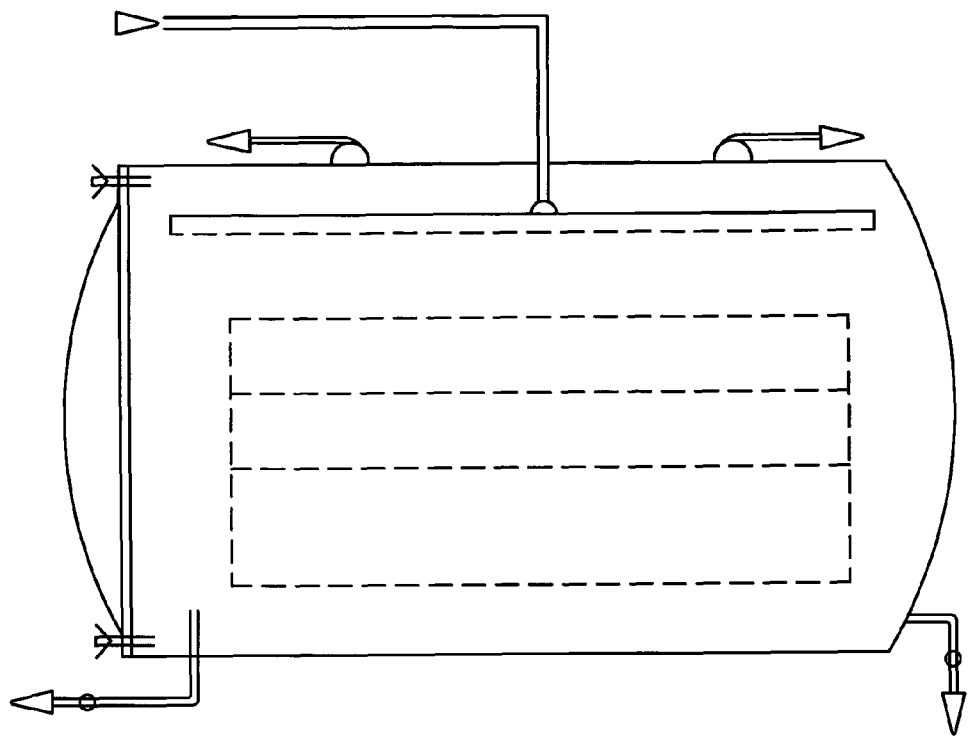
FIG. 6(a)  Water Supply
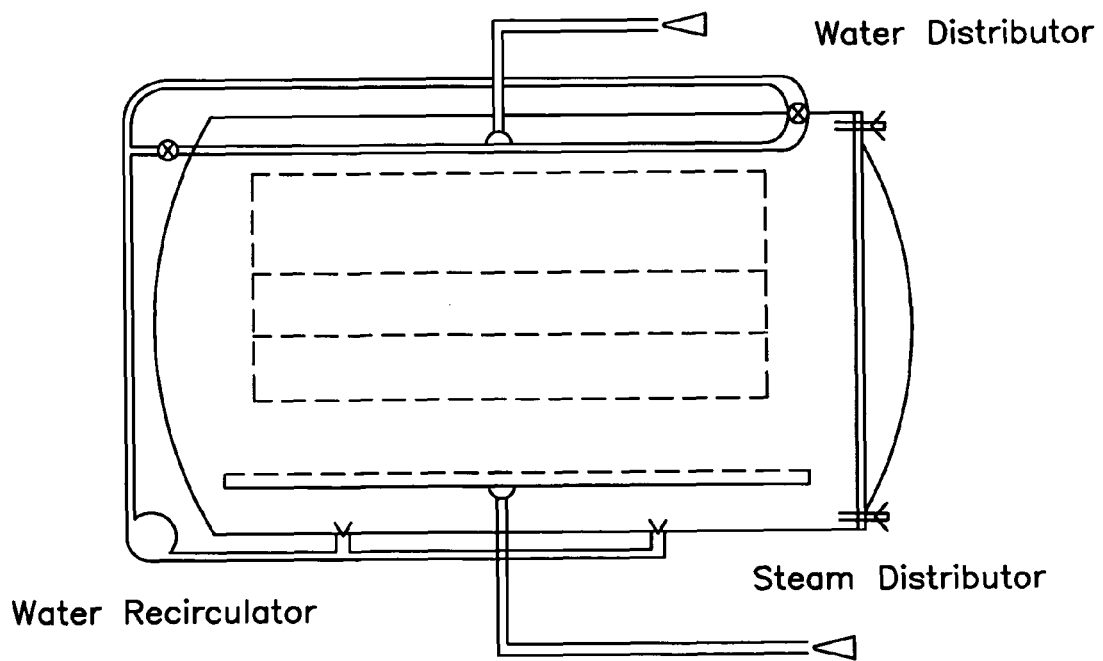
FIG. 6(b)  Steam Supply

EVALUATING BACTERIAL LETHALITY OF CONTAINERIZED FOOD PRODUCTION

RELATED APPLICATION

This application claims the benefit of U.S. Provisional Patent Application Ser. No. 60/674,610 filed Apr. 25, 2005.

INTRODUCTION

This invention relates to procedures and means for evaluating effectiveness of bacterial-lethality, following batch-processed containerized food production operations, including aseptic-packaging of containerized foods, in preparation for marketing. More particularly, this invention is concerned with methods and apparatus for evaluating results of batch-food processing, in determining whether such food production, as processed and containerized, is safe for non-refrigerated marketing.

OBJECTS OF THE INVENTION

A primary object is reliably evaluating bacterial-lethality resulting from thermal-processing carried-out in conjunction with containerized batch-food production operations.

A specific object is providing for test-ampoule constituents for evaluating bacterial-lethality results of such batch-food thermal-processing.

A related object involves preparatory steps which facilitate thermal-processing which is protective of batch-food quality while such food is being prepared for non-refrigerated marketing.

A further related object provides methods and means for correlating bacterial-lethality test determinations with bacterial-lethality experienced by the batch-food being processed.

Another object extends such evaluations to batch-food operational systems, such as:

(i) aseptic system flow-type thermal processing, followed by containerization in aseptic containers;

(ii) a coordinated batch-food preparation system in which thermal-processing is substantially augmented and completed by impelled movement of sealed suitably-rigid containerized food through selected travel-path of retort-equipment; and (iii) a coordinated batch-food processing system for foods in substantially non-rigid packages which remain essentially immobile, as positioned for augmented and completed thermal-processing, in an enlarged retort chamber.

Other objects and a fuller understanding of the invention are presented in the following description and claims, taken in conjunction with the accompanying drawings, in which:

BRIEF DESCRIPTION OF THE FIGURES

FIG. 2 is a schematic graphical presentation for describing selective analyses and preparatory steps of the invention for regulating thermal-processing containerized batch-food production operations;

FIGS. 3(a) and 3(b) are elevational views for describing substantially-rigid types of test-ampoules as preferably used in testing suitably-rigid type containers in accordance with the invention;

FIGS. 4(a) through 4(f) are perspective views for describing fabrication of pliable polymeric test-ampoules of as preferably used in testing with substantially non-rigid batch-processed food production packaging, in accordance with the invention; in which:

FIG. 4(a) shows sealing at one longitudinal-end of elongated-tubular configuration formed from non-rigid polymeric sheet material;

FIG. 4(b) depicts later-described constituents as added within the polymeric tubular-configuration of FIG. 4(a), so as to enable fabricating multiple individual test-ampoules of the invention from such polymeric tubular configuration, and FIGS. 4(c)-4(f) are perspective views for describing equipment and steps as combined for fabricating multiple such pliable polymeric test-ampoules of the invention, in which:

FIG. 4(c) shows heat-source apparatus, for sealing one longitudinal-end of such polymeric elongated tubular-configuration as shown in FIG. 4(a), and providing for follow-up forming multiple individual test-ampoules of the invention for use in relatively soft-packaged batch-food production operations in accordance with the invention;

FIG. 4(d) shows operational-closing of the heat-sealer structural apparatus of FIG. 4(c) for describing specifics of the heat-sealing of the polymeric material, as relied-on, in the invention, for forming individual test-ampoules containing test constituents; while FIGS. 4(e) and 4(f) are perspective views for describing individual test-ampoules of the invention and their fabrication from such polymeric elongated-tubular configuration;

FIG. 5(a) combines an elevational cross sectional view of a rigid sheet-metal one-piece can body, and a top plan view of its end-closure, as preferred for use of rigid-type test-ampoules of the invention, during containerized batch-food processing production operations;

FIGS. 6(a) and 6(b) are schematic cross-sectional views of retort means for describing augmenting and/or completing thermal-processing of non-rigid polymeric pouches, and partially-pliable batch-food containers of the type shown in FIGS. 5(d) and 5(e), while such packaging remains substantially-stationary, in accordance with the invention within an enlarged temperature-controlled retort-chamber;

DETAILED DESCRIPTION OF THE INVENTION

Figure 1:
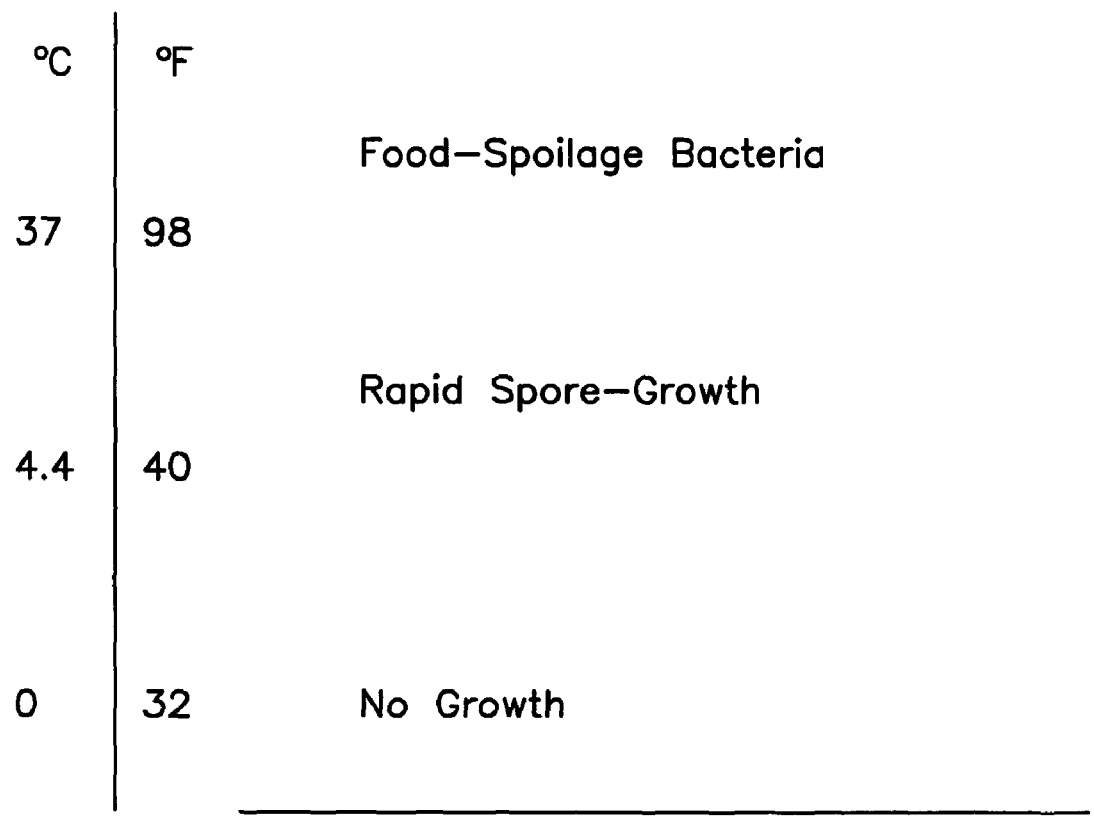
FIG. 1 is a schematic graphical presentation for describing relevant temperature ranges for facilitating correlating test evaluations, within test-ampoules of the invention, with bacterial-lethality experienced within batch-food processed containers resulting from production operations.

In accordance with long-established prior practice for non-refrigerated food marketing, batch-processed containerized rigid sheet metal cans have been and continue to be, utilized. Those cans have been, and continue to be, retained in non-refrigerated inventory for extended time periods, extending to four weeks, or more. Such detention periods have been, and are, relied on for detecting bulging or leaking mechanical faults due to the presence of food-spoilage bacteria, which had not been destroyed by the thermal-processing during batch-processed containerized food production-operations.

The structural strength of currently-used rigid flat-rolled sheet-metal cans has been augmented by the use of one-piece can bodies which are free of both a side-wall seam and a bottom end-wall seam. However, such one-piece can bodies make it more likely that increased time intervals will be required for inventory-storage-time, in order to detect mechanical faults, such as "end-bulging", responsive to the presence of live food-spoilage bacteria.

Concepts of the present invention are directed to chemically-based evaluations of the effectiveness of thermal-processing, rather than awaiting occurrence of mechanical faults or failures during inventory storage. Such test evaluations, as taught herein, are carried out significantly more promptly, eliminating the prior practice which relied on extended-inventory storage-times for "mechanical" failure to determine whether thermally-processed contents of batch containerized foods were free of live food-spoilage bacteria.

The test-evaluations of the invention significantly expedite determining whether thermally-processed containerized food-production is safe for non-refrigerated marketing. The presence or absence of live spore-forming bacteria is determined chemically; and, a biological-indicator verification of microbial-biocidal status of the packaged food can also be made available. Present teachings determine whether rigid-sheet metal containers, and/or whether the new, and newly developing, non-refrigerated food packages, which largely utilize polymeric materials, for convenient microwave-oven heating of opened-packs, are safe for non-refrigerated marketing; and such determination is made substantially more concurrently with their production.

Whether thermal-processing as selected for particular containerized production-operations has, or has not, accomplished "destruction" of food-spoilage bacteria, is determined; and, more specifically, that determines whether timed-exposure, at a selected elevated-temperature, as part of thermal-processing production operations has, or has not, accomplished desired bacterial-lethality, so as to enable non-refrigerated marketing. Also, such determinations are achieved in accordance with the invention, free of extended storage requirements relying on a mechanical-failure indication of food-spoilage.

As taught, and provided for herein, microbial-biocidal test-ampoules and test methods of the invention are correlated with batch-food production operations for expediting detection of the presence or absence of spore-producing bacteria in containerized-food production. Further, a biological-indication for verification of biocidal-status is also preferably provided by establishing incubation conditions for test-means of the invention. Biological-indication comprises a readily-accepted supplemental verification of the microbial-biocidal status; as to whether, or not, the particularly-processed containerized food production is safe for non-refrigerated marketing; and, in addition, whether such food-production processing should continue is determined in a more timely manner than available when waiting for mechanical failures.

In practice of the invention individual test-ampoules are fabricated to have sufficient internal volume so as to safely contain selected live-bacteria, plus liquid-state test constituents, as disclosed herein, during exposure to various temperatures levels. Bacteria for the test means are selected, as taught herein, to have thermal-response characteristics which correlate with characteristics of bacteria associated with the containerized foods being processed.

Other contributions of the invention are concerned with:

(i) constructional and configurational concepts for certain test-ampoules suitable for current and market-developing packaging;

(ii) coordinating requirements for qualifying particular test-ampoules for use with particular-developing types of containers for non-refrigerated marketing; and (iii) with optimizing test-ampoules and testing methods for differing types of batch-food production operations.

Use of rigid frangible materials, with properties similar to glass, in the manufacture of test-ampoules of the invention; or, for practice of testing methods of the invention, have purposefully been limited to suitably-rigid containerized food production. That purpose is to preclude any potential that particulate, from frangible materials, from becoming part of containerized food production. In addition, new pliable test-ampoules as disclosed herein, are provided for newly-developing soft-external packaging.

Test-ampoules and testing methods of the invention have also been devised to be adaptable to widen application of developing types of containerized production-operations, such as:

(i) aseptic-flow control which includes high-temperature-short-time (HT-ST) thermal-processing of the food, followed by containerization in customized internal treatment of aseptic containers;

(ii) thermal-processing including in-line impelled movement of suitably-rigid containers, through defined travel-path retort-heating equipment, and (iii) augmented or completed thermal-processing, in which softer packaging is maintained substantially-immobile in an enlarged, controllably-heated, retort chamber.

Qualifying characteristics have been established for polymeric materials for fabricating soft test-ampoules of the invention and for carrying-out testing methods of the invention. Such qualifying characteristics include:

(i) that test-ampoule materials do not react chemically with the internal test-constituents of a functionally-complete test-ampoule, at any temperature encountered during production processing or during testing, (ii) that test-ampoule structural materials be made available in a form, and with sufficient visual clarity, for promptly evaluating test results, visually (iii) that such test-ampoule materials provide sufficient strength for confined sealing of selected constituents of a test-ampoule, and, (iv) that such test-ampoule materials be capable of maintaining desired strength at elevated temperature(s) during production processing of selected foods and testing thereof.

Additional concepts of the invention identify selections for correlating bacterial-lethality characteristics within the test-ampoule with the bacterial-lethality characteristics of food spoilage bacteria in the food(s) being processed. As taught herein, the bacteria for the test-means are selected to respond in a manner correlated with bacteria associated with the foods being processed. A predominate microorganism, considered important to be eliminated in most batch-processed containerized-food production for non-refrigerated marketing, is *Clostridium botulinum* (BOT); which is a micro-organism that produces spores, and which is capable of producing toxic results in certain such foods. These testing predeterminations and preparations are described, in greater detail in relation to later occurring FIGURES.

FIGS. 1 and 2 present graphical data for describing temperature-range concepts relating to the test-means, and to utilization of such test means, as part of the invention. More specifically, such data is used to facilitate correlating adequate thermal-processing of a containerized food production system, with measurable and timely results in utilizing the test-methods and test-ampoule-means of the invention.

Thermal-processing combines selecting an elevated-temperature and a timed-exposure at such temperature, in order to achieve bacterial-lethality; that is, to achieve "biocidal destruction" of spore-producing food-spoilage bacteria associated with the food(s) being processed. "Destruction" of bacteria, as used herein, means not only killing those bacteria; but, also, destroying any capability:

(i) for reproducing by division of individual bacterial cells, or (ii) for producing-spores by those bacteria.

The graphical data of FIG. 1 also facilitates selecting culturing temperature(s) to be utilized in a biological-indication-test for bacterial-lethality effectiveness which verifies a chemical-change indication, available more directly following completion of such exposure of a test-ampoule. The data of FIG. 1 also contributes to identifying proper storage for test-ampoules prior to actual usage; that is, storage at a temperature, where no bacterial spore germination and no bacteria-cell growth can take place, with the bacteria selected for the test constituents.

It is emphasized that culturing temperature for test-ampoule constituents:

(a) can differ greatly from thermal-processing temperatures of production-operations for destroying bacteria; however, spore culturing temperatures, (b) can readily-overlap with non-refrigerated temperatures encountered within containerized-production during non-refrigerated marketing; and, also (c) can differ greatly from the temperatures at which assembled test-ampoule constituents of the invention should be held, prior to designated usage; such latter temperature range is selected so as to maintain and sustain test-capabilities of such ampoule constituents for testing of subsequent production-processing operations.

As part of the invention, bacteria are selected to:

(i) correlate thermal-processing response of:

(a) bacteria contained in the test constituents, with (b) bacteria contained in food(s) being processed.

Further, preparatory testing concepts of the invention also involve analyzing for properties, such as the pH level of the food, or foods, for specified batch-food processed containerized-production operations.

In describing analytical preparatory steps of the invention, and their function(s), reference is also made to the graphical data of FIG. 2. Constituents for a test-ampoule of the invention are also selected so as to provide for favorable measurable microbial-action; for example: a desired bacterial-lethality response, internally of the ampoule, which is correlated with the thermal-processing results, due to destruction of spore-producing bacteria contained in, or associated with the food(s) being thermally-processed, as part of the batch-food containerized production operations.

Predeterminations of inherent pH values, for the differing types of foods being processed are taken into account for thermal-processing; so as to provide more efficient thermal-processing; and, so as to facilitate testing the effectiveness of the thermal-processing. *Clostridium botulinum* (BOT) bacteria have been chosen as the most versatile bacteria across a range of packaged products being developed for non-refrigerated marketing. Such that, pH values can also be relevant in considering differing non-refrigerated shipping and marketing conditions. BOT bacteria are particularly useful where safety of the consumer is being considered; that is, a major consideration herein, and a main concern is human safety.

For example; *Clostridium botulinum* will not grow in high-acid foods; such that: thermal-processing and testing of high-acid foods takes into consideration other health or taste factors. A pH level 4.6, for tomatoes, separates high acid foods from low acid foods; and, low acid foods, such as asparagus, meat and fish, having higher pH numbers, require higher levels of thermal-processing to provide for desired microbial-biocidal-action for non-refrigerated marketing.

Also, as taught herein, constituents for test-ampoules are selected to have characteristics similar to characteristics of the batch-processed food(s) of the containerized production-operations. However, also to be recognized, is that many low-acid containerized foods would qualify as a culturing medium for live bacteria, if any, under the non-refrigerated temperatures normally-encountered during warehousing or shipping for marketing. Recognition of such culturing capabilities is taken into account in the planning for and in test evaluations of bacterial-lethality, following production operation.

Thermal-processing combines both elevated-temperature, and sufficient time at that temperature, for destruction of live spore-producing bacteria associated with a food, or a combination of foods as confronted when soups are being processed. An overall objective of the invention is to provide for, and to test for, adequate thermal-processing conditions of food(s) being processed; while also providing for microbial-biocidal action on container interior surfaces; so as to be similar to the effect on the contents of test-ampoules, as selectively positioned in monitoring-containers. The food-spoilage bacteria for the test-ampoules are selected and confined within test-ampoules of the invention, so as to react similarly to bacteria encountered throughout batch-food thermal-processing of various specified containerized production-operations.

In addition, the configuration, constructional-materials, and the size of a test-ampoule of the invention are selected to take into account the size and texture of the food(s) to be processed, as well as the type of packaging. Combining those measures facilitates accurately evaluating the effectiveness of thermal-processing, in destroying food-spoilage bacteria, for reasons of human safety.

In addition, however, those objectives also help to provide promptly-available test-evaluations of results of the thermal-processing; which can help to prevent over-processing in ongoing operations. That is, accurate and timely evaluation of effective thermal-processing operations can help to avoid the undesirable flavor, texture, or appearance of food(s), which can be expected from over-processing; and, can be helpful in planning for selected production operations on similar foods.

Relatively high acid-level foods, which exhibit relatively low pH numbers extending up to about four point six (4.6), enable diminishing thermal-processing for non-refrigerated packaging of those foods, so as to enable concentrating on non-toxic characteristics for containerization in selected production operations. Relatively high salt or sugar content can also inhibit microbial-growth so as to diminish thermal-processing for toxicity requirements. Prompt availability and ease of obtaining lethality test-results, as taught herein, can be helpful in more promptly determining whether the thermal-processing for destruction of bacteria, should properly be increased or decreased in on-going production-operation; or, in planning, similarly-processed production-operation.

For spore-destruction purposes lower-acidity level foods require higher-levels of thermal processing, which can be a factor in selecting the type of batch-food production thermal-processing. An increase in thermal-processing temperature level, and/or the time-duration at that thermal-processing temperature, can be combined. The objective is proper thermal-processing so as to enable accurate and prompt evaluation of intended destruction of food-spoilage bacteria in batch-processed foods, and on container-interiors selected for thermally-processed containerized-production operations.

Analyses of such preparatory determinations, as pH level(s) for the food(s) enable more accurate correlation of test-ampoule results with actual results on the food(s) being processed and containerized. And, by making test results available more promptly, enables fine-tuning of thermal-processing to be carried out more promptly, or accomplished in a timely manner for similarly-planned production operations. For example: numerical pH values are taken into account:

(i) in assembly of test-ampoules,
(ii) in applying testing methods of the invention, and,
(iii) in helping to promptly and accurately verify destruction, or lack thereof, of spore-producing food-spoilage bacteria of specific food(s) during selected batch-processing containerized-production operations for non-refrigerated marketing.

In carrying out the invention, selected spore-producing food-spoilage bacteria are confined within an individual-sealed test-ampoule so as to be exposed to thermal-processing of the food production-operation. Test constituents are selected to facilitate a visual-type of evaluation of the batch-food production operations; which can be available promptly for properly limiting thermal-processing for both safety; and, for protecting food quality in similarly planned processing operations. A further available test-evaluation, for verifying the microbial-biocidal status utilizes a "biological-indication", in which spore-culturing solution within the test-ampoules, enables culturing conditions to be promptly carried-out relying upon the color-change indications; however, both such evaluations are carried out while all contents remain confined within the test-ampoule; avoiding any chance of contamination which could effect test results.

Further, a "positioning-arrangement" concept of the invention which substantially increases production capabilities and diminishes losses, involves limiting the number of evaluations of containerized test-ampoules which should be, or need be made; while, at the same time enabling extension of results of a limited number of positionally-arranged monitoring-container test-ampoule evaluations to enable accurately evaluating a substantially-greater number of containers, associated in the containerized production operations, by the positional arrangement concept of containers with test means.

A sealed test-ampoule, containing test constituents is immersed in food-contents of such a selected limited number of individual monitoring-containers. Such monitoring-containers which individually confine a test-ampoule of the invention, are positionally-located in particular, during retort-operations, in a manner so as to precisely identify a substantially greater number of associated-containers. Such associated-containers are positioned intermediate such monitoring containers which include test-means, so as to experience substantially the same thermal-processing as such positionally-arranged monitoring containers.

After cooling down from thermal-processing conditions, individual test-ampoules from individual positionally-selected monitoring-containers, are accountably removed, from a positionally-identified monitoring-container for testing. As taught herein, selective-positioning of such individual monitoring-containers in preparation for and during thermal-processing, is used to identify such substantially-greater number of associated-containers which experience substantially the same thermal-processing, because of positioning, for example in-line, intermediate of monitoring containers during production operations. Those concepts increase the range, and the extent of measured results, notwithstanding that a substantially lower number of test-ampoules from such individual monitoring-containers need be evaluated; which is also described in more detail in relation to later FIGURES.

FIGS. 3(a) and 3(b) each present an elevational view of rigid-type test-ampoule means, for use in substantially-rigid monitoring-containers. Such rigid-glass exterior test-ampoules, permit use in thermal-processing liquids. Each such rigid-type test ampoule contains spore culturing nutrients, a pH indicator, and the selected bacteria.

If bacteria survive, provisions are made for prompt visual-detection of color-change of such liquid constituents. Also, provision is made for a subsequent biological-indication of microbial-status, by establishing culturing conditions for the test-ampoule; while all its contents remain sealed within the exterior container. Rigid-type test-ampoules are available from SGM Biotech, Inc. of 10 Evergreen Drive, Suite #E, Bozeman, Mont.; owner of the present application. A rigid-type test-ampoule as shown in FIG. 3(a) is a MAGNAAMP® indicator; and 3(b) presents a STERILAMP® indicator, available from the same source. Both contain test ingredients providing for a color-change initial indication of processing effectiveness; and, also, provide for subsequent biological-indication of microbial status, following exposure of the test-ampoule to culturing conditions. Use of such rigid-type test-ampoules of the types shown in FIGS. 3(a) and 3(b), is preferably limited to suitably-rigid type processed-food containers.

Test-ampoules, which are free of any concerns fracturing, as described later herein, are provided for softer-packaged batch-processed food production operations. The description of FIGS. 4(a) through 4(f) relate to selecting materials for, and fabricating pliable non-rigid test-ampoules; which are particularly for use with foods containerized in other than the suitably-rigid type containers, as described herein.

Figure 4A:
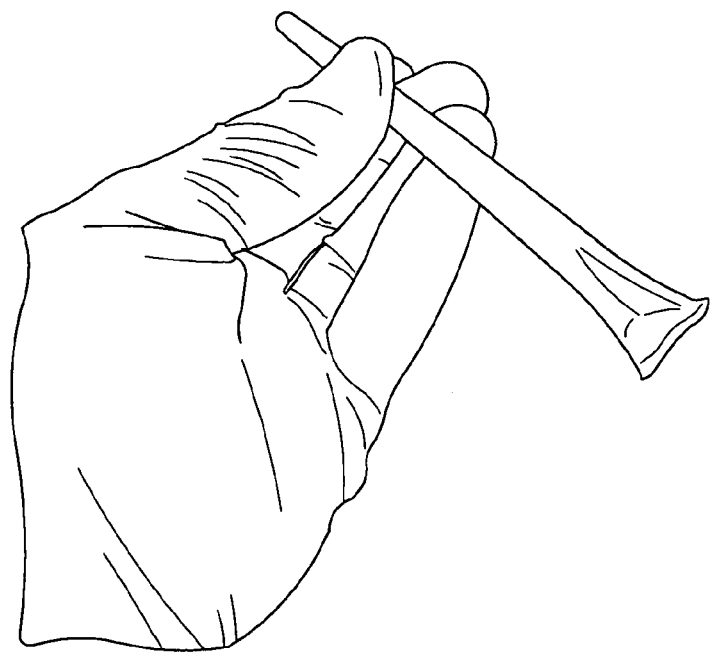

In FIG. 4(a), a thin-flexible, clear polymeric sheet material, which provides the necessary strength, and visual clarity characteristics, is initially fabricated so as to present an elongated hollow tubular configuration. One end of that elongated configuration is sealed by use of a heat-sealing apparatus, shown in later FIGURES, which establishes a thin sealing line, across the tubular width, contiguous to one longitudinal end of the elongated hollow-tubular configuration, as shown in FIG. 4(a). Such thin sealing line should be protected by heat-molding at portions similarly-extending widthwise; and preferably located contiguous on each longitudinally-located side of such sealing line. Such heat-molded protection of a sealing line can also be, and preferably, is used in fabricating individual test-ampoules, as shown in later FIGURES, positioned along the length of the elongated tubular configuration.

Figure 4B:
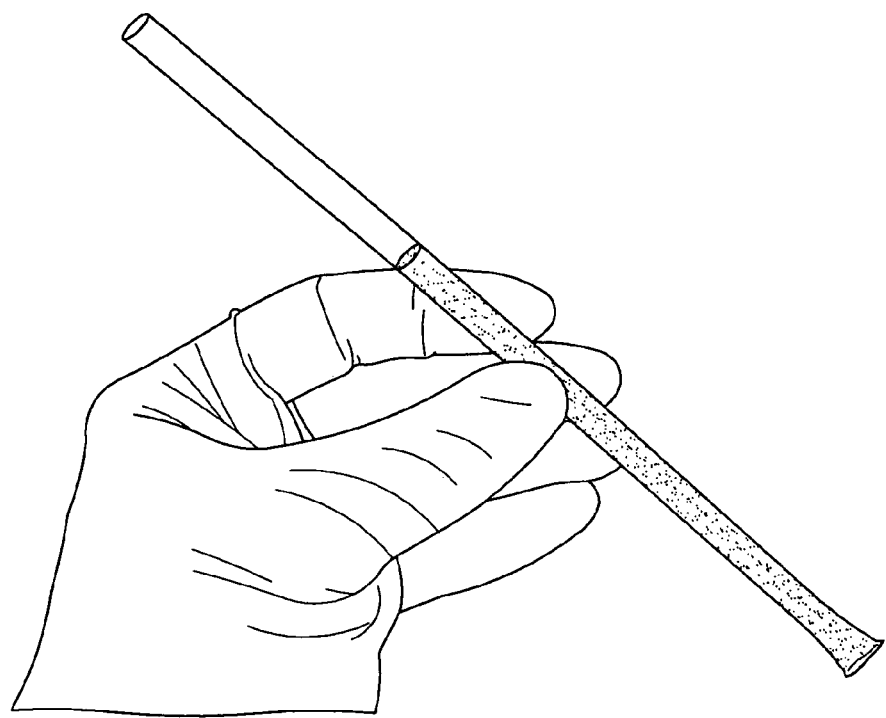

As shown in FIG. 4(b), the interior of the elongated flexible-polymeric tubular configuration is selectively filled with test-ampoule contents. The latter include;

(i) liquid-state constituents as mentioned above and later described in more detail, (ii) selected spore-producing food-spoilage bacteria (such as BOT), and (iii) means provided for detecting a chemical change in of such liquid contents, if any bacteria survive the thermal-processing; the functional interrelationship of each of the above is described, in more detail, later herein.

Figure 4C:
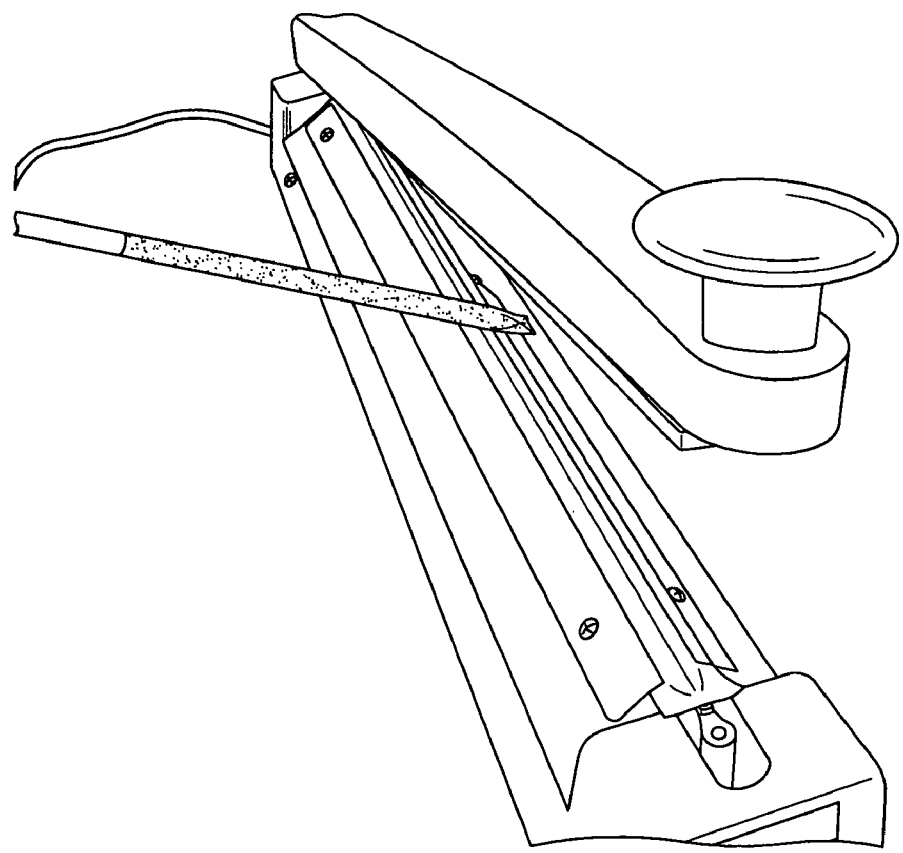

Sufficient contents are provided in the elongated tubular configuration of FIG. 4(b), so as to enable fabricating a selected number of polymeric test-ampoules. The steps for fabricating individual polymeric test ampoules are depicted in subsequent FIGURES. FIG. 4(c) shows a type of heat-impulse apparatus which can be utilized for sealing ends; as well as a selected number of individual polymeric test-ampoules; such as "Impulse Sealer"; is available from:

Uline Shipping Supply Specialist
2105 S. Lakeside Dr.
Waukegan, Ill. 60085

Figure 4D:
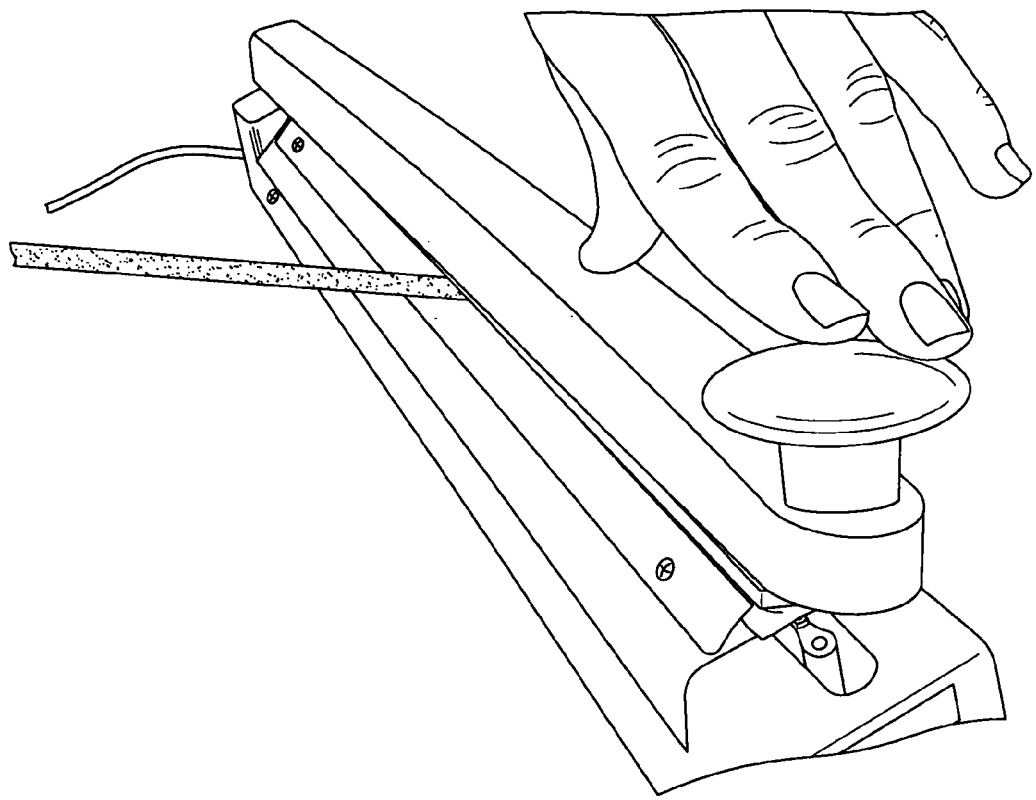

As seen in FIG. 4(d) closing of such a heat-sealer apparatus establishes a sealing line for test contents of each polymeric test-ampoule. FIG. 4(a) presents a perspective view of a distal-end formed sealing line; which is preferably protected by a contiguous heat-molded portion, on each longitudinal-side of the individual heat-sealing line. FIG. 4(c) shows use of the heat-sealing apparatus for fabricating an individual test-ampoule of the type to be provided contiguous to such sealed longitudinal end of the tubular configuration.

Figure 4E:
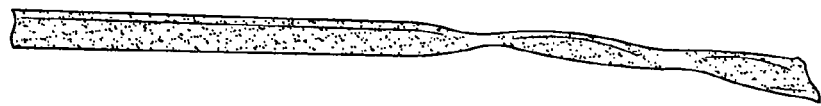

FIG. 4(d) shows operation of the heat sealer apparatus. Each individual test-ampoule, as shown in FIG. 4(e) is substantially filled with the named liquid-state constituents and other contents. A minor amount of air, which had been dissolved in the solution, can also be present, as shown, notwithstanding that a previous, at least partial, evacuation of liquid contents had been carried-out. However, such limited presence of air can be useful dependent on the type bacteria used in the test-means.

Air (oxygen) is present during preparation of foods at least in-part during the above-named containerized production-operations. With dissolved air present for the subsequent evaluations utilizing such polymeric test-ampoules, as shown in FIGS. 4(e) and (f); such test-ampoules and the foods being processed are thus correlated in that respect.

Figure 4F:
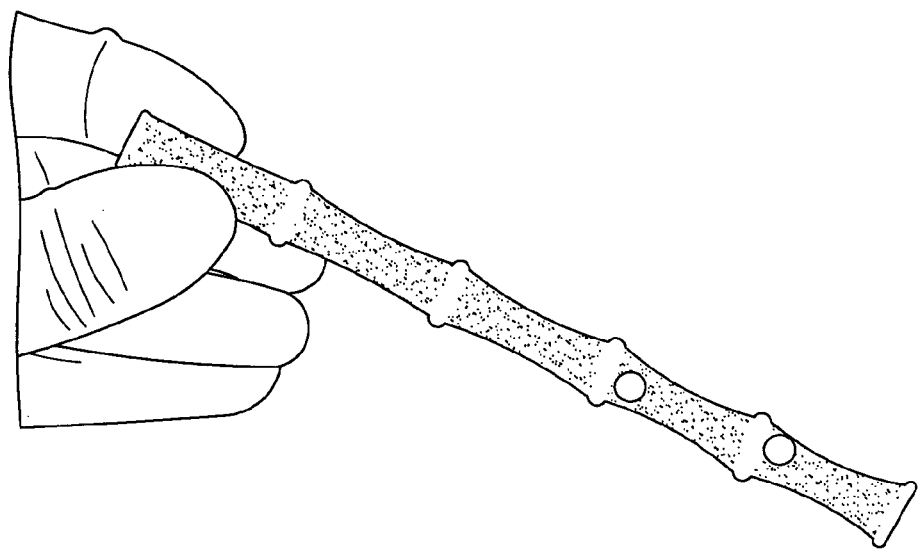

The elongated tubular configuration of FIG. 4(b) is sealed at selected intervals, along its length, to form individual test-ampoules as shown in FIG. 4(f); each sealed width-wise between individual ampoules; and, at longitudinal-ends of such elongated configuration which forms multiple test-ampoules. Such thin sealing lines, for an individual-ampoule, are preferably additionally protected by an adjacent heat-molded portion extending width-wise on each longitudinal side of a test-ampoule sealing line; such heat molded portions facilitate later proper separation of individual ampoules along the length of the tubular configuration. Each test-ampoule confines, internally, the desired volume of culturing medium, an indicator/detector responsive to chemical-change, if live bacteria or spores survive the thermal processing; and, selected spore-producing food-spoilage bacteria.

Internal-capacity for such test constituents is selected in a range of about one cubic centimeter ($cm^3$) to about two cubic centimeters ($cm^3$) for use with the popular, individual consumer-sized, containers. Larger-sized test-ampoules can be fabricated when useful for larger containers of the type used in supplying commercial eateries, and the like.

Representative stable thermoplastic polymers, available as thin, flexible-film for fabricating test-ampoules include:

Polypropylene (PP)
Polymethylpentene (PMP)
Polyvinyl Chloride (PVC)
Polysulphone (PSP)
Polyamide (such as Nylon 6-6);
and, combinations thereof.

Such pliable test-ampoules could also be fabricated from newly-developing polymers, or other combinations of polymers, which have similar chemical-resistances and fabricating characteristics as above-described. Any such added or newly developing polymer can be selected, and qualified, based on the above-disclosed criteria and the physical and mechanical data provided herein, relating to: test-ampoules capacity, heat-stability for desired thermal-processing, and other designated characteristics, which enable evaluating the status of thermally-processed containerized food production operations for non-refrigerated marketing.

A liquid carbohydrate-based culturing-medium is selected, for the earlier described rigid and pliable polymeric-tubular test-ampoules. That medium will support growth of live spore-producing thermophile food-spoilage bacteria within a test-ampoule; if any survive the thermal-processing of the selected production-operations. Constituents for a test-ampoule culturing medium, comprise selections of carbohydrates, sugar, starch, etc., which can be formulated to correspond to "culturing" characteristics of the food(s) being processed and evaluated. Related objectives are to;

(i) provide for correlated selections of bacteria;
(ii) with substantially the same culturing properties for both:
(a) the test-ampoule constituents, and
(b) the containerized food; so as to:
(iii) correlate accuracy and promptness of test evaluations for bacterial-lethality.

A preferred culturing medium for test-ampoules of the invention contains:

| | Constituent: | Gram(s)/Liter |
|---|---|---|
| (i) | Glucose | 5.0 |
| (ii) | Tryptone | 8.5 |
| (iii) | Soytone | 1.5 |
| (iv) | Soluble Starch | 1.0 |
| (v) | Yeast Extract | 0.5; |
| (vi) | Casamino Acids | 4.0 | and, in addition (vii) a pH indicator/detector, as selected from the group consisting of:
(a) Bromcresol Purple,
(b) Bromthymol Blue, or
(c) Phenol Red.

Bromcresol Purple is frequently selected because of distinct coloration-effects; and, for freedom from side effects on remaining test-ampoule constituents; or, on the culturing reaction relied on for the biological-indication of microbial-biocidal status. Bromcresol Purple is selected at a level of about 0.0024 Gram/Liter, of the above culturing-medium for a test ampoule of the invention. Bromcresol Purple establishes the color purple for the test-ampoule constituents. A chemical-change in acidification, resulting in microbial growth changes in color to yellow in response to the presence of live spore-producing bacteria, if any; such change in acidification is also utilized for a biological-indication of microbial status; that is, bacterial-growth responding to culturing conditions causes acidification.

A representative culturing temperature, for such biological indications, is above about 55° C. to 60° C., (about 131° F. to 140° F.). Such temperature is maintained in order to establish culturing conditions for such test ampoule, after removal from a monitoring-container. Dual test-results can then be obtained; and, as briefly described earlier; those results on selected bacteria within a test-ampoule, as submersed in a monitoring-container, can be correlated with thermal-processing results on in-line additional containers identified by the positionally arranged containers. For example, if any live bacteria survive, both of the above microbial-action determinations correlate results within the test-ampoules of monitoring containers positionally-arranged to identify numerous additional containers by the location of the monitoring-containers from which the test-ampoules are taken.

Thus a limited number of individual monitoring-containers, each with an individual test-ampoule, are utilized by proper-placement during production processing to identify a significantly greater number of "associated-containers" which experience substantially the same thermal-processing. Pre-placements of such monitoring-containers in-line when utilizing retort-means for thermal processing facilitates the accuracy of identifying the substantial greater number of "associated" containers. Aseptic-flow processing depends on placement of monitoring-containers in the flow-line.

For example, numerically-extended results can be achieved, by placements at both the leading and the trailing ends of a selected in-line flow path. Such placements identify a substantially-greater number of intermediate-located associated-containers, which as exposed to substantially the same thermal-processing, are evaluated by individual test-ampoule, immersed in such strategically-located individual monitoring-containers, located at the leading and at the trailing ends of each such in-line travel path.

It should be noted that an in-line monitoring-container at the trailing-end of a designated flow path, can be utilized to provide an evaluation for the leading end of the next succeeding in-line travel-path; that is, such a trailing-end test-ampoule can be used as the leading-edge indicator, by selectively establishing a position for a monitoring-container at the trailing end of the next in-line travel path.

Individual test-ampoules are removed from monitoring-containers following cool-down subsequent to the thermal-processing of the selected production system; so as to enable obtaining a visual color-change; due for example to the Bromcresol purple. If bacteria have survived, such a change in color to yellow, due to inadequate exposure during thermal processing operations, can be determined as visually-aided in a matter of hours; and, a biological-indication of microbial-status can be obtained by utilizing culturing conditions. That is, surviving spore-producing bacteria within such a test-ampoule produce acid if the thermal-processing has not been adequate; thus, providing for both color change indication and a biological-indication responsive to culturing-conditions.

Visual detection of color change, or absence thereof, visually-unaided, can be detected within about forty-eight (48) hours of such production-operations. A biological-indication verification of microbial status can be aided by detection means responsive to change in hydrogen-ion concentration. Test-ampoules of the invention combine selected spore-producing food-spoilage bacteria, and detector/indicators responsive to microbial action, if any bacteria-cell growth, or any bacterial spore germination occurs following the thermal-processing. Multiple determinations of microbial-biocidal experience are available. For example, chemical-reaction color-change in the test-ampoule solution indicates survival of bacteria. Destruction of food-spoilage bacteria can be selectively determined by visually observing such a color-change in accordance with the invention; and, further, by biological-indication of response by surviving bacteria; detecting increased hydrogen-ion content can be used to expedite that biological-indication.

If the determined status indicates that bacteria in at least one test-ampoule, of a pair identifying an in-line travel path, have survived the thermal-processing; in addition to (i) finding and eliminating the cause of such inadequate-thermal processing, (ii) identifying and preventing distribution of associated-containers, which were located so as to also have been inadequately thermally-processed, are also required.

Establishing that such associated-containers experience the same thermal-processing in an aseptic-flow system involves timed flow-line introduction of a monitoring-container into the flow; so as to position a test-ampoule at each leading and trailing end of a designated-length in-line flow-path, so as to determine thermal-processing experience during such aseptic-flow. Subsequent evaluation of a test-ampoule from a monitoring-container at both the leading and trailing ends of such timed in-line flow-path, provides for proper bacterial-lethality evaluation of intermediately-located-containers.

Production-operations using agitation-type retort-equipment, as well as the thermal-processing of an aseptic-flow system, each can involve strategically-positioning a designated individual monitoring-container, at both the leading and the trailing ends of a designated in-line travel path for associated-containers. Such travel paths are selected, designated, and used to establish that a substantially-greater number of intermediately-located-containers, experience substantially the same thermal processing as the strategically-positioned monitoring-containers. Individual test-ampoules for both the leading-end and trailing end monitoring container are then evaluated; and, that sequencing can then be continued, as earlier described.

Figure 5:
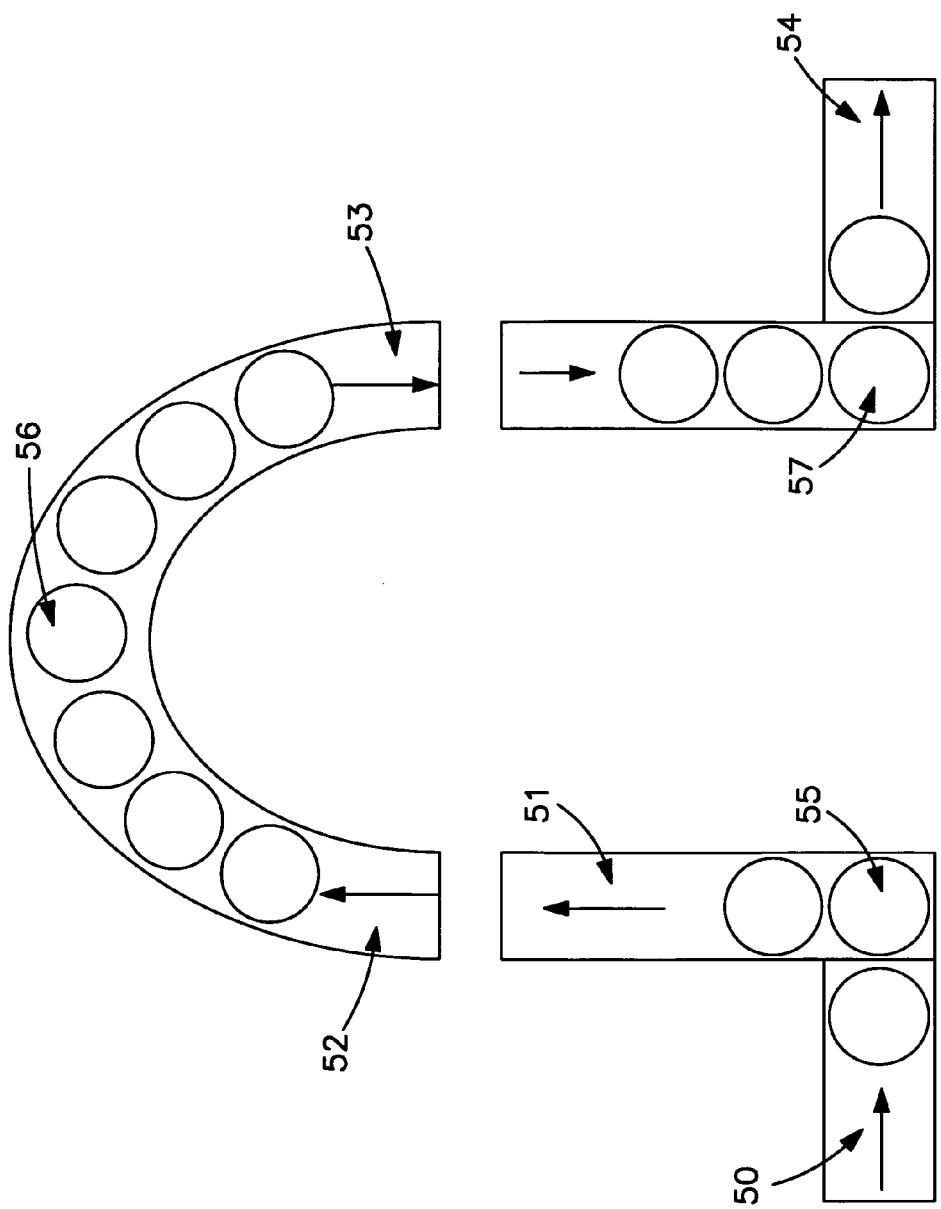
FIG. 5 is a schematic view of multiple-travel-path retort equipment for impelled-movement, for describing concepts of the invention involving positioning a minimal number of rigid-type monitoring-containers, each containing a test-ampoule, so as to facilitate determining thermal-processing effectiveness on a substantially greater number of containers, which are free of a test-ampoule, while being positionally-associated with monitoring-containers.

Agitation-type retort-equipment, as shown schematically in FIG. 5, is largely used for containers having rigid characteristics which are capable of assisting in impelling movement along in-line travel-paths, within such equipment. For example, a rolling-action is available with cylindrical-configuration rigid flat-rolled sheet metal cans, which increases the capacity of the retort equipment. Assistance in impelling movement, is used in the agitation-type retort-equipment layout of FIG. 5; and, causes agitated movement of contents within containers. The latter helps to make the intended thermal-processing more uniform on container contents; and, on the contents of individual test-ampoules. A rigid-type test-ampoule of a type described in relation to FIGS. 3(a) or (b), can be used in an individual monitoring-container at the leading-end with another individual monitoring container at the trailing-end of such an in-line travel-path.

In agitation-type retort-equipment as shown, passageways are preferably heated with saturated steam; although pressurized super-heated water could be provided for, and could be used. Saturated steam temperatures are suitably selected for the containerized food, starting at 212° F. (100° C.). Pressurized super-heated water temperatures start above 212° F. (100° C.) and can extend in a range of to about 225° F. (107.2° C.) to 250° F. (121.1° C.). Also, individual containers each with a one-piece substantially-rigid polymeric can body and a single rigid-sheet metal end closure, can be supported for vertical-travel through vertically-oriented heated-passageway in-line travel paths.

The length of a pre-determined in-line travel-path is selected, based on disclosed methods, in which strategically-placed monitoring-containers, each containing an individual test-ampoule, can be relied on to determine the status of associated-containers traveling substantially-identical travel paths. As disclosed above, a monitoring-container is placed at both the leading and the trailing ends of such a designated in-line travel path.

In FIG. 5, individual containers can enter the retort-equipment along the path indicated by directional arrow 50; and, travel upwardly along the direction of arrow 51. The containers continue to travel into a curved path indicated by directional arrow 52; then, downwardly in the direction of arrow 53 toward the exit direction indicated by arrow 54. Cylindrical configuration sheet-metal sealed-cans, which can be readily rotated about their central axis during such travel, are preferred for use in such changing-direction travel-paths.

In order to have analyses of monitoring-containers with immersed test-ampoules correlate with thermal-processing of a plurality of in-line associated-containers, strategic-placement of monitoring-containers is established by analyzing such criteria as:

(i) rate of thermal-processing to be provided by retort-equipment;

(ii) pH level of the food(s) being processed; and (iii) the type of food-spoilage bacteria, associated with the food being processed.

Rate of thermal-processing involves in-line travel time, which can be reliably estimated, during preparatory analyses steps of available heat and line-speed, so as to determine the number of containers which can be thermally-processed during a selected timed-interval in a numerically-designated travel-path. Overall capacity of retort-equipment for cylindrical sheet-metal cans, can be designed with significant variety. As an example, cylindrical containers in a selected travel-path(s) could extend in a range from about one hundred to five times that number, by properly coordinated batch-food production operations with retort thermal-processing operations.

In operating retort-equipment schematically-shown in FIG. 5, at location 55 a monitoring-container, with immersed test-ampoules could reach thermal-processing temperature at that entrance to the travel-path(s) selected for the retort-equipment. A time-at-temperature could be selected for an in-line travel-path to complete thermal-processing; which could extend over an initial travel-path length of about one hundred cans; extending to a centrally-located position, as shown at 56. A container removed at 56 would comprise the leading travel-path monitoring-container; and, one hundred in-line cans later, the travel-path trailing-end monitoring-container is available. Evaluations of those two monitoring-containers would then determine the status of the significantly-greater number of associated-containers in the selected travel-path.

Where increased thermal-processing is required, the monitoring-containers with test-ampoules, and the associated-containers could travel an extended-length path of such illustrated retort-equipment apparatus; for example, extending to exiting location 57. Dependent on the above-described retort-equipment operating criteria, locations for monitoring-containers with an immersed test-ampoules, could then be located at the entrance to, and exit from, such an extended travel-path, which would extend thermal-processing time; and, the microbial-status of an increased number of intermediately-located associated-containers would be available.

Figure 5B:
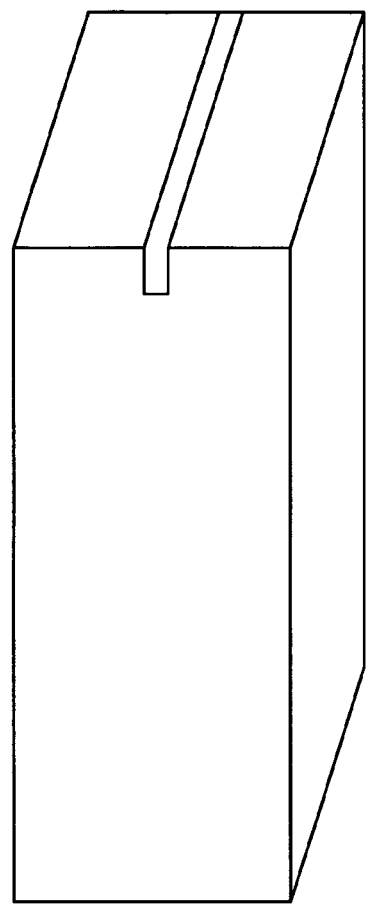
FIG. 5(b) is a schematic elevational view of non-rigid completed packaging, combining polymeric laminated metallic foil and cardboard, for describing when and how to test for non-refrigerated marketing as carried out in accordance with the invention.

FIG. 5(b) is a perspective view of a flat-sided composite-material used largely for aseptically-processed packaged products such soups; as well as larger quart-size soy-milk packaged for non-refrigerated marketing; until opened. Externally-visible cardboard surfaces for those types of composite-material containers, positional thin-metallic foil internally of the composite for protection of the product; and, both the interior and exterior surfaces of such foil are laminated with one, or more, polymeric-film layers. Instructions for use, and for describing the contents of the package, are on the exterior surfaces the cardboard; which is also protected by at least a single polymeric layer.

Figure 5C:
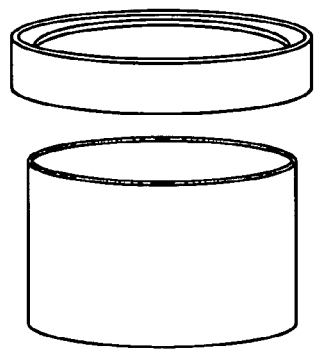
FIG. 5(c) is a schematic view of completed packaging, combining a one-piece substantially-rigid polymeric can body which defines a single-opening for an easy-open sheet metal end closure, for describing testing as carried out in accordance with the invention.

Cup-shaped configurations for substantially-rigid containers can be fabricated with a one-piece rigid-polymer can body, with a rigid-flat-rolled sheet metal "easy-open" end closure; as represented by FIG. 5(c); which could utilize in-line travel-path configuration providing for vertically-movable support structure adapted to that configuration, in retort-equipment of the type described in relation to FIG. 5. other-configuration containers which combine a rigid-type polymeric cup-shape, with an "easy-open" rigid flat-rolled sheet metal end closure; can also be accommodated. For content consumption purposes, the open-end is covered, after removal of the easy-open end, with a plastic cover which enables microwave heating. In addition to retort-cooker thermal processing as described in relation to FIG. 5, another production-operation option for such containers is use of aseptic-flow capable of handling selected-characteristics and cut-sizes suitable for containerization in aseptic-containers.

Figure 5D:
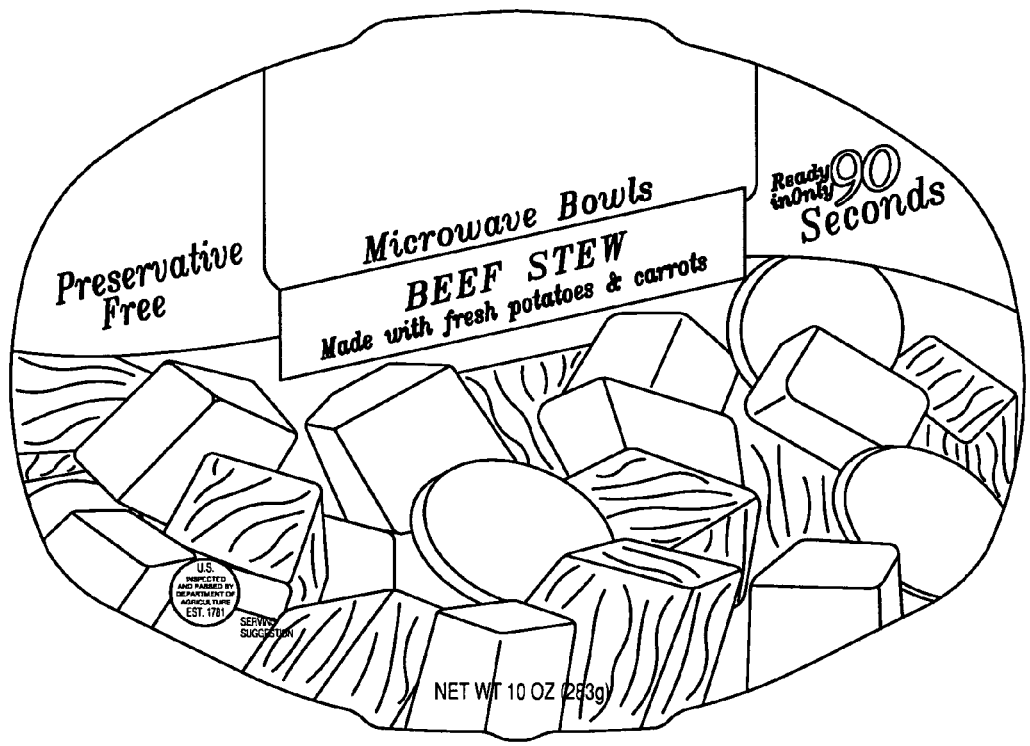
FIGS. 5(d) and 5(e) are schematic views of relatively-thin partially-pliable polymeric serving-tray and pan-like container configurations, which are sealed with thin polymeric sheeting, for describing testing utilizing non-rigid polymeric-tubular-configuration test-ampoules of the invention.
Figure 5E:
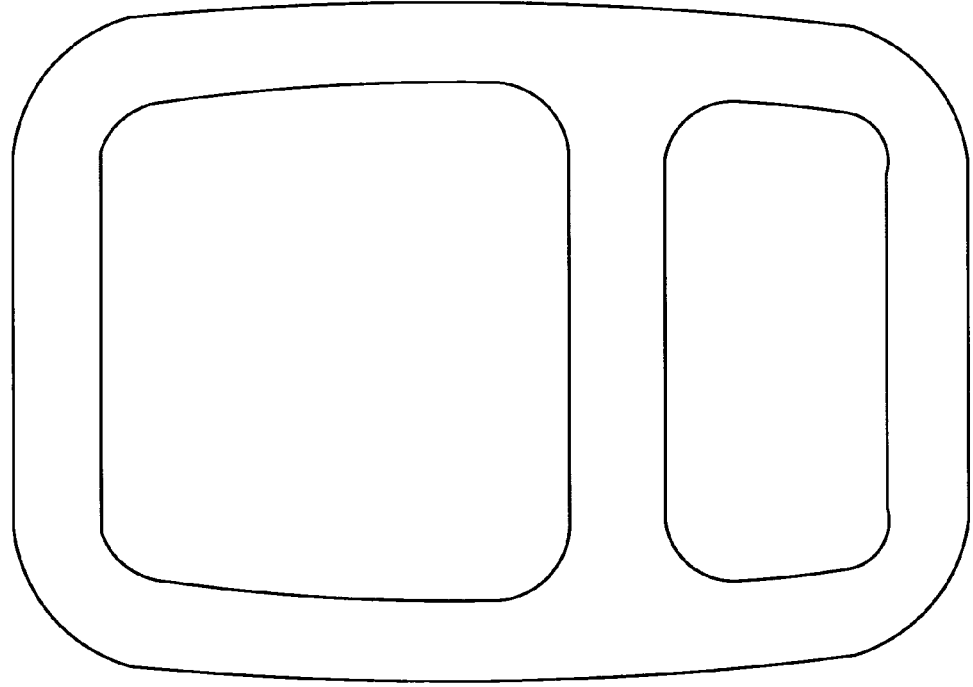

FIGS. 5(d) and 5(e) are plan views of packaging utilizing a relatively-thinner less-rigid polymeric-pan for receiving food contents during food-preparation operations. The upper surface of such a pan is sealed with polymeric sheeting. Such less-rigid pans can present a single compartment as shown in FIG. 5 (d); or, multiple compartments as shown in FIG. 5 (e). Such packaging concepts of FIGS. 5(d) and 5(e) broadly rely on described testing principles of the invention for evaluating thermal-processing. However, "stationary-type" retort-equipment shown in FIGS. 6 (a) and 6 (b), as taught herein, can be utilized. Such chamber-type retort-equipment has been devised, in particular, for handling such low-cost above-described semi-rigid polymeric shallow-pans sealed with a polymeric sheet cover. Such stationary retort-equipment, can also be used for non-rigid pouch-type laminated polymer containers which are later packaged, in a cardboard shell, which describes contents, presents instructions for non-refrigerated marketing, and instructions for subsequent preparation and/or usage of food contents.

No inter-active movement-impelling force between containers is relied-on in such stationary-type of retort-equipment. Such semi-rigid sealed shallow-pans, and/or such special laminated-polymer pouches, are supported on individual vertically-spaced shelves, as shown in FIG. 6(a). Such vertically-spaced shelves can be mounted on a single-rack, which substantially fills the entire stationary retort-chamber. The size of the rack, the chamber, and entrance and/or exit doors, are established to enable movement of a full-rack into and out of a stationary-type retort-chamber for thermal-processing of the selected production-operations.

A heated-jacket is preferred, for such stationary-type retort-equipment, which facilitates completing thermal-processing in shorter time-cycles. The stacked shelves and rack are preferably fabricated to facilitate chamber entrance and exit; and, to match the internal configuration of the retort-cooker chamber. That provides for single-step full loading and unloading of the chamber; and, minimizes heat-loss between cycles.

Use of saturated-steam in the thermal-processing concepts of FIG. 6(a), with heated-jacket walls help to desired readiness, and, to help provide for uniformity of thermal-processing at the selected temperature. Saturated steam is supplied at 212° F. (100° C.) to the chamber by one, or more, elongated rows of steam inlets along the full length of the upper portion of the chamber. Steam inlet provisions are coordinated so as to facilitate removal of air, and any condensate of the steam, under control of thermo-static valves which are located at one or more locations along the lower portion of the stationary-positioning retort-chamber. Directional-control of the saturated-steam can be implemented by baffles where helpful. Additional steps, such as positioning larger containers near upper portions of the chamber, can be taken to help to provide desired uniformity throughout the chamber in completing thermal-processing of the selected production-processing. A contributing factor to uniformity involves introducing steam, at upper locations, so as to help to drive the heavier air toward the lower portion of the chamber; for exit from the chamber through thermostatic valve(s) at lower locations. That augments heating of the load and expedites accomplishment of the "time-at-temperature" portion of thermal-processing.

Those measures are utilized to facilitate establishing and maintaining a selected uniform thermal-processing temperature throughout the chamber during thermal-processing; and, to facilitate re-establishing such conditions for each retort thermal-processing batch cycle. Timing of thermal-processing is selected depending on the food(s) being processed as discussed earlier, in practice, saturated steam is provided at a temperature of at least 212° F. (100° C.) for a designated time duration.

The chamber of FIG. 6(b) provides for use of water heated with superheated steam; and provides for holding the packaging in place at various levels of the rack which occupies substantially the full chamber thermal-processing for the selected production operation is carried out with steam at about 225° F. (107.2° C.) to 250° F. (121.1° C.).

In FIGS. 6(a) and 6(b), monitoring-containers with immersed test-ampoule means are positioned at predetermined chamber locations on the rack. Those locations are predetermined based on achieving the desired uniformity of thermal-processing of associated-containers. That uniformity is implemented by selecting easier-to-heat packaging for difficult-to-heat locations. Such locations are generally furthest removed from the introduction of the heat-source, which can differ for the chambers of FIGS. 6(a) and 6(b).

Measures have been devised for introducing pressurized steam for super-heating water, by withdrawing vapors at upper portions of the FIG. 6(b) chamber for augmenting heating from lower portions of the chamber for achieving substantially-uniform thermal-processing for all shelf-mounted containers while in the chamber shown in FIG. 6(b).

Test-ampoule teachings of the invention are applicable to thermally-processing foods which contain a designated amount of free moisture. That is, present testing methods and use of the test-ampoules, as disclosed herein, are not required and are not utilized for dry-packaged ingredients; such as: dried sauces or dried-soup ingredients. Those types of contents are generally prepared, for consumption, by adding water or milk, followed by a boiling-type cooking in preparation for eating.

Food-spoilage bacteria do not multiply or produce spores in the absence of an abundance of free-moisture. Test-ampoules and testing methods, as described herein are not utilized in the absence of free-moisture which enables spore growth; and, also, facilitates destruction of bacteria, as described herein.

Soft-packaging pouches free of any rigid portion, can also be readily thermally-processed in stationary retort-equipment, as shown in FIG. 6(a) using saturated-steam. Such non-rigid soft-packaging, after verification of thermal-processing by use of selectively-positioned monitoring-container(s), is then further packaged, individually, or in groups, in semi-rigid light-weight cardboard casings which include identifying labeling and instructions for usage. Such casings are also helpful in making store shelf displays and in providing protection for the soft-packaging.

Aseptic-flow thermal processing relies on a high temperature (293° F. to 320° F.) (145° C. to 160° C.) short flow-line time; with selected materials relied on for sterilizing the interior of an aseptic container. An aseptic-system sequence of steps is described further in the text of the box-diagram flow chart of FIG. 7. Cream-style soups such as broccoli or chicken are readily flow-processed prior to being fed into aseptic containers as fabricated, for example, within a metallic foil liner with polymer coating(s) on inside and outside surfaces of a boxed contents, as described in relation to FIG. 5(b). Contents which include sized pieces of meat or vegetable can also be aseptic flow-processed for substantially-rigid containers as shown in FIG. 5(c). Test-ampoules are periodically immersed along an in-line aseptic-flow path starting with initiation of aseptic-flow thermal-processing; and, periodically thereafter, depending on the designated flow-rate, in aseptic monitoring-containers before sealing of these containers.

Locations for monitoring-container(s), with immersed test-ampoules, are selectively identified and designated based on the in-line aseptic-flow production rate. In that manner, a selected number of associated-containers is established for an in-line flow-path, by positioning a test-ampoule for disposition in a designated monitoring-container; with such a designated monitoring-container being located at the leading and/or trailing ends of each such in-line flow-path, for identifying a plurality of intermediately-located associated-containers.

Control of aseptic-system flow enables tagging the locations for monitoring-containers, each of which includes a test-ampoule immersed in food-contents. Subsequent to aseptic flow processing and aseptic containerization, test-ampoules of such designated monitoring-containers can be evaluated for microbial-action which can be measured in several ways, as described earlier; relying on surviving bacteria, if any, increasing the acidity of the liquid test contents so as to produce a visibly-detectable color-change; and, which can also be determined by electrometrically or spectroscopically measuring hydrogen-ion activity. Constituents of an individual test-ampoule, as removed from such designated-location monitoring-containers, which are positioned to establish status of associated-containers, as previously described.

Figure 7:
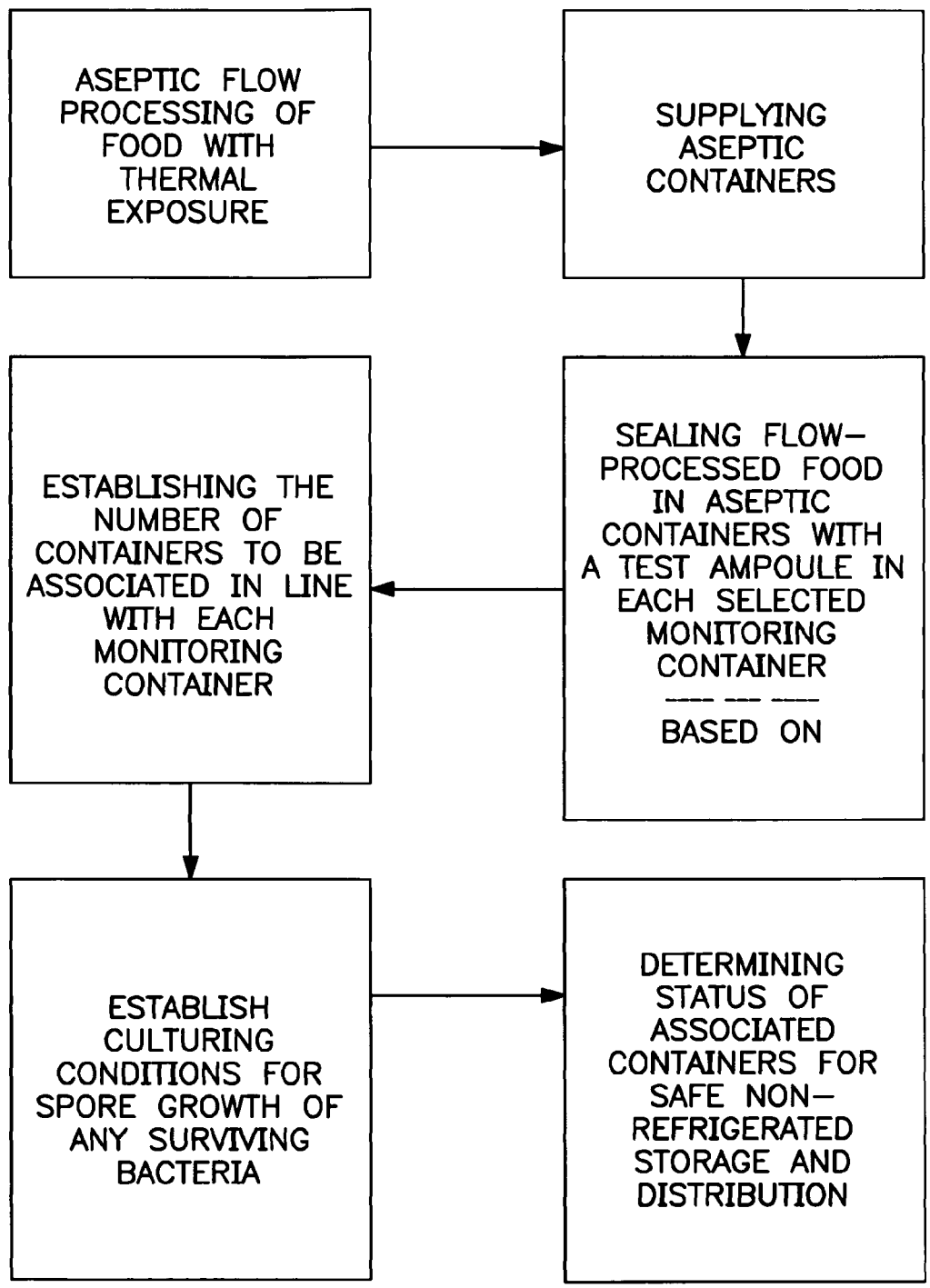
FIG. 7 is a box-diagram flow chart for describing aseptic-flow system operations in which thermal-processing is followed by containerization in aseptic containers, while utilizing a concept of the invention, for minimizing test ampoule evaluations required for effectiveness of such aseptic production operations.
Figure 8:
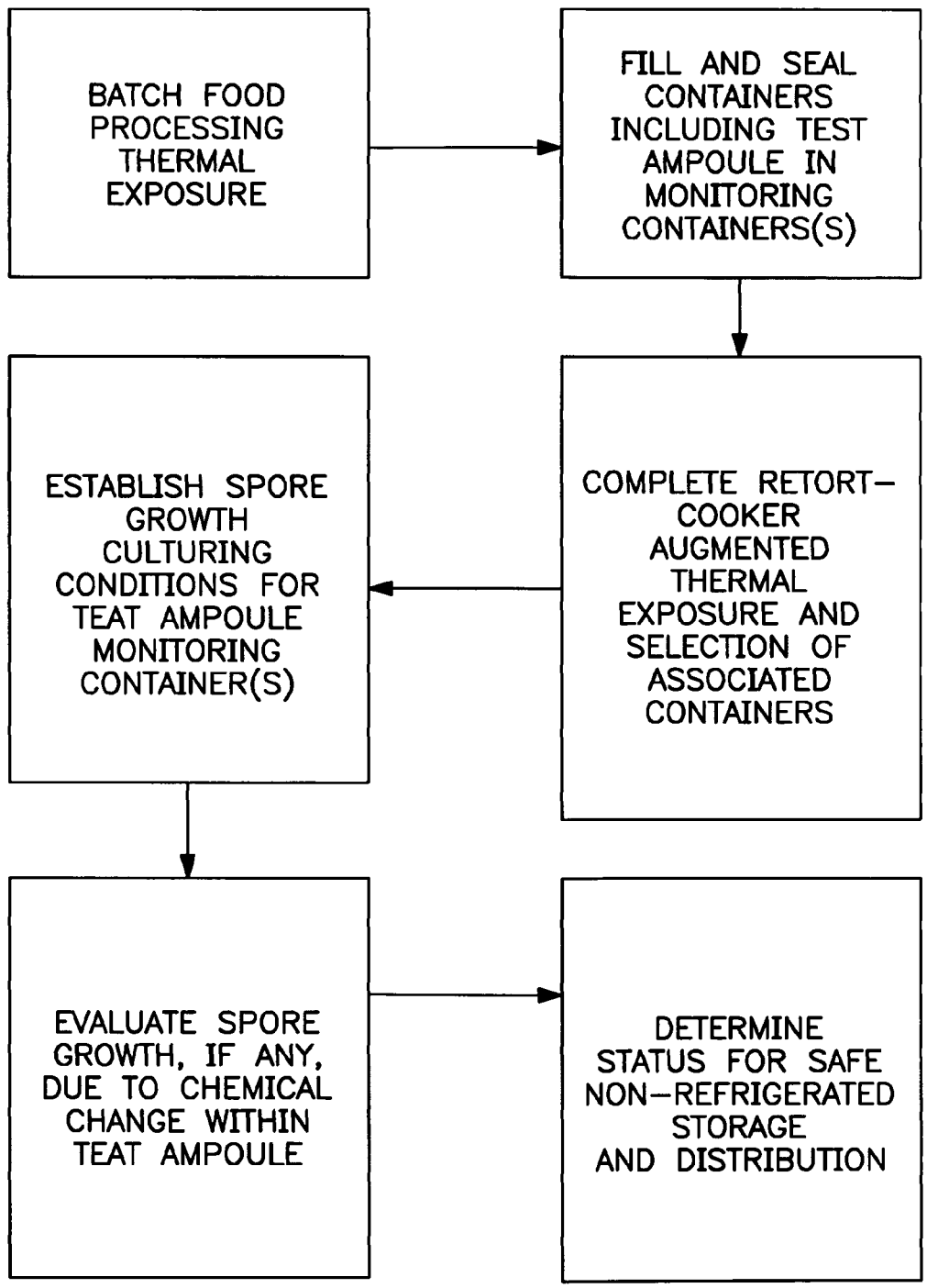
FIG. 8 is a box-diagram flow-chart for describing added testing systems of the invention and providing for minimizing the number of tests, in accordance with the invention, for evaluating thermal-processing effectiveness of added production operations for safe non-refrigerated marketing.

The descriptions of steps for the systems of FIGS. 7 and 8, facilitate accurate analyses of the status of associated containers, based on analyses of immersed test-ampoules in strategically-located or timed-interval flow locations of monitoring-containers in FIG. 2. As described above, a monitoring-container is located at the leading and trailing ends of designated, flow paths so as to verify the thermal-processing status of a substantially greater number of intermediate associated-containers in the flow. That concept minimizes the number of containers which need be unsealed for retrieval of a test-ampoule, for verifying the status of a substantially greater number of containers in the aseptic production-operations.

Containerized food-production operations using retort-equipment can take into account thermal-exposure, if any, carried out during a food preparation stage, while fulfilling or augmenting a major portion of the thermal-processing utilizing subsequent retort operations, as described further in the box-diagram flow-chart sequence of FIG. 8. Those operations provide for evaluation of results in associated-containers by relying on strategically-located monitoring-containers each including a test-ampoule for evaluating effectiveness of the microbial-biocidal action, which is applicable to a plurality of associated-containers, as disclosed above.

Embodiments of the invention have been described with a degree of particularity. However, it should be recognized that other non-refrigerated packaging, minor changes in test-method steps, test-ampoule-structures, configurations, combinations of polymers, test-ampoule constituents, or selection of the bacteria, for making additional evaluations are made accessible, in the light of the above teachings. Therefore, reference should be made to the accompanying claims and to the above terminology for evaluating the valid scope of the invention based on the claimed combination of materials, procedures, and methods, as disclosed and described above.

What is claimed is:

1. A process for determining effectiveness of timed elevated temperature thermal processing of batch-processed containerized food production operations including in-line aseptic flow-processing for aseptic containerization production operations, for evaluating whether it is safe for non-refrigerated marketing, comprising
    (A) providing sealed test-ampoules for evaluating bacterial lethality effectiveness of elevated temperature thermal processing on food spoilage bacteria associated with batch-processed food production for determining whether safe for non-refrigerated marketing, the test-ampoules having confined therein a selected food spoilage spore-producing bacteria, in a liquid spore-culturing medium, wherein the test-ampoules are non-rigid polymeric test-ampoules constructed and arranged from a non-rigid polymeric sheet material which is capable of withstanding elevated temperature thermal processing as part of such batch food containerized production operations, while maintaining visual clarity during such thermal processing and subsequent evaluation of bacterial lethality effectiveness,
    (B) placing individual test-ampoules in a limited number of food containers for use in containerized food production operations,
    (C) carrying out timed elevated temperature thermal processing as part of containerized food production operations, and
    (D) detecting a microbial-biocidal status of the spore-producing bacteria sealed within the individual test-ampoules for assessing biocidal results achieved on such spore-producing bacteria associated with the foods subjected to the containerized food production operations, characterized in that step (D) is effected by detecting chemical change due to microbial action of surviving live bacteria, if any, in the test-ampoules by means of a pH indicator contained in the liquid spore-culturing medium.

2. A process according to claim 1 wherein the pH indicator in the test-ampoule is selected to respond to microbial action of surviving bacteria, if any, by exhibiting color-change responsive microbial action due to inadequacy of thermal processing during such food production operations, so as to be visually observable after cool-down following completion of such food production operations, and in which the liquid spore-culturing medium provides for biological indication of microbial status, following exposure of the test-ampoule to bacterial incubation conditions.

3. A process according to claim 2 in which the spore-culturing medium comprises:
    (i) Glucose,
    (ii) Tryptone,
    (iii) Soytone,
    (iv) Soluble Starch,
    (v) Yeast Extract, and
    (vi) Casamino Acids;
and the pH indicator comprises Bromcresol Purple.

4. A process according to claim 1 wherein the non-rigid polymeric sheet material is:
    (i) substantially transparent to electromagnetic energy wavelengths in a visible light spectrum, and
    (ii) non-reactive chemically with contents of the test-ampoule, during
        (a) batch-food production operations,
        (b) testing thereof, and
        (c) during storage prior to usage at less than spore-culturing condition temperature.

5. A process according to claim 4 in which the polymeric sheet material is a thermoplastic polymer.

6. A process according to claim 5 in which the polymeric sheet material is selected from the group consisting of:
    (i) Polypropylene,
    (ii) Polymethylpentene,
    (iii) Polyvinyl Chloride,
    (iv) Polysulphone,
    (v) Nylon, and
    (vi) combinations thereof.

7. A process according to claim 1 wherein the test-ampoules are positioned in a limited number of the food containers for monitoring thermal processing so as to leave a substantially greater number of food containers which are free of test-ampoules, and subjecting all the food containers to substantially the same thermal processing experience so as to enable:
    (i) evaluating bacterial lethality by relying on test constituents in the limited number of the food containers with test-ampoules positioned for
    (ii) determining whether the greater number of remaining food containers are safe for non-refrigerated marketing.

8. A process according to claim 7 including providing for biological indication of microbial status following an incubation period, subsequent to production line operations, by
    (i) establishing culturing conditions for each of the individual test-ampoules designated for monitoring thermal processing,
    (ii) incubating the test-ampoules, and
    (iii) verifying the microbial-biocidal status of the test-ampoules after incubation which thereby correlates to a microbial-biocidal status of the substantially greater number of food containers experiencing substantially the same thermal processing as the food containers containing test-ampoules.

9. A process according to claim 8 wherein verifying the microbial-biocidal status of the limited number of the food containers with test-ampoules therein is selected from the group consisting of
    (a) measuring hydrogen-ion activity with a spectroscopic means, and
    (b) measuring hydrogen-ion activity with an electrometric means.

* * * * *